US006824512B2

(12) United States Patent
Warkentin et al.

(10) Patent No.: US 6,824,512 B2
(45) Date of Patent: Nov. 30, 2004

(54) COMMUNICATIONS SYSTEM FOR AN IMPLANTABLE DEVICE AND A DRUG DISPENSER

(75) Inventors: Dwight H. Warkentin, Arden Hills, MN (US); Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 242 days.

(21) Appl. No.: 10/123,958

(22) Filed: Apr. 17, 2002

(65) Prior Publication Data

US 2002/0111542 A1 Aug. 15, 2002

Related U.S. Application Data

(63) Continuation of application No. 09/475,709, filed on Dec. 30, 1999, now Pat. No. 6,471,645.

(51) Int. Cl.[7] .................................................. A61B 5/00
(52) U.S. Cl. ........................ 600/300; 128/903; 128/920; 607/60
(58) Field of Search ................................. 600/300–301, 600/508; 607/29–30, 59–60; 604/66, 65; 128/898, 903, 904, 905, 920–925; 340/573, 870, 309; 206/531, 533

(56) References Cited

U.S. PATENT DOCUMENTS

| 4,360,126 A | 11/1982 | Martindale et al. ............. 221/2 |
| 4,494,950 A | 1/1985 | Fischell ........................ 605/66 |
| 4,617,557 A | * 10/1986 | Gordon .................... 340/309.7 |
| 4,768,176 A | 8/1988 | Kehr et al. .................... 368/10 |
| 4,768,177 A | 8/1988 | Kehr et al. .................... 368/10 |
| 4,987,897 A | 1/1991 | Funke .................. 128/419 PG |
| 5,200,891 A | 4/1993 | Kehr et al. ............. 365/413.01 |
| 5,642,731 A | 7/1997 | Kehr ........................... 128/630 |
| 5,752,235 A | 5/1998 | Kehr et al. ..................... 705/3 |
| 5,752,976 A | 5/1998 | Duffin et al. .................. 607/32 |
| 5,950,632 A | * 9/1999 | Reber et al. ................. 128/898 |
| 5,954,641 A | 9/1999 | Kehr et al. ................... 600/300 |
| 5,971,594 A | 10/1999 | Sahai et al. ............ 364/479.12 |
| 6,294,999 B1 | * 9/2001 | Yarin et al. ............... 340/573.1 |

FOREIGN PATENT DOCUMENTS

| EP | 0 526 166 A2 | 2/1993 | ........... G05F/15/42 |
| EP | 1 022 035 A1 | 7/2000 | .......... A61N/1/372 |

OTHER PUBLICATIONS

MEDIMONITOR internet information, InforMedix, Inc., Georgetowne Park, 5920 Hubbard Drive, Rocville, MD 20852, ph. 301.984.1566, fax: 301.816.0907, "http://www.informedix.com/print–site.htm".
Product Sheet, Advantor Corporation, "http://www.advantor.com/products.htm".

* cited by examiner

Primary Examiner—Max F. Hindenburg
Assistant Examiner—Michael Astorino
(74) Attorney, Agent, or Firm—Girma Wolde-Michael; Paul H. McDowall

(57) ABSTRACT

A closed loop system for monitoring drug dose, intake and effectiveness includes a pill dispenser in data communications with at least one implantable medical device. The system is preferably implemented in a web-enabled environment in which a remote data center communicates with the implantable devices (IMDs) in a patient via a programmer or the pill dispenser. Th data center includes high speed computers and databases relating to patient history and device information. A physician or clinician may access the remote data center to review and monitor the IMDs remotely. More specifically, the IMDs are adapted to chronically monitor the pill dispenser to thereby log and document drug dose, patient compliance with prescriptive regimens and as well to monitor drug efficacy in the patient. The system further provides a dynamic drug management system, compatible with a web-enabled interactive data communication environment, that accurately monitors dose and specific drug effectiveness in a patient to enhance patient care.

9 Claims, 4 Drawing Sheets

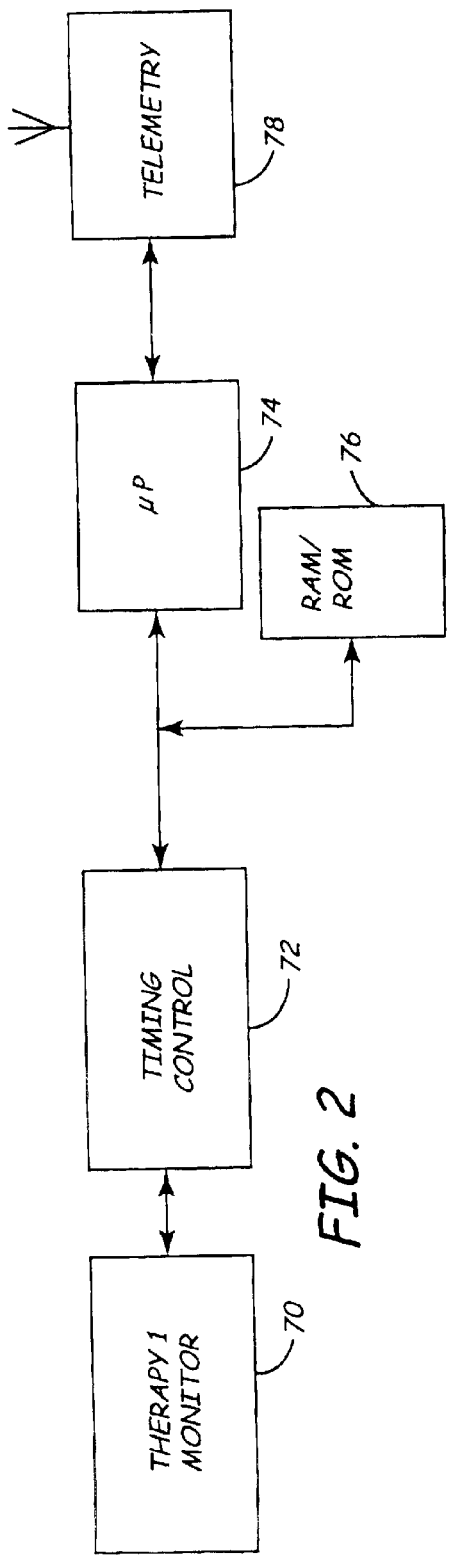
FIG. 2
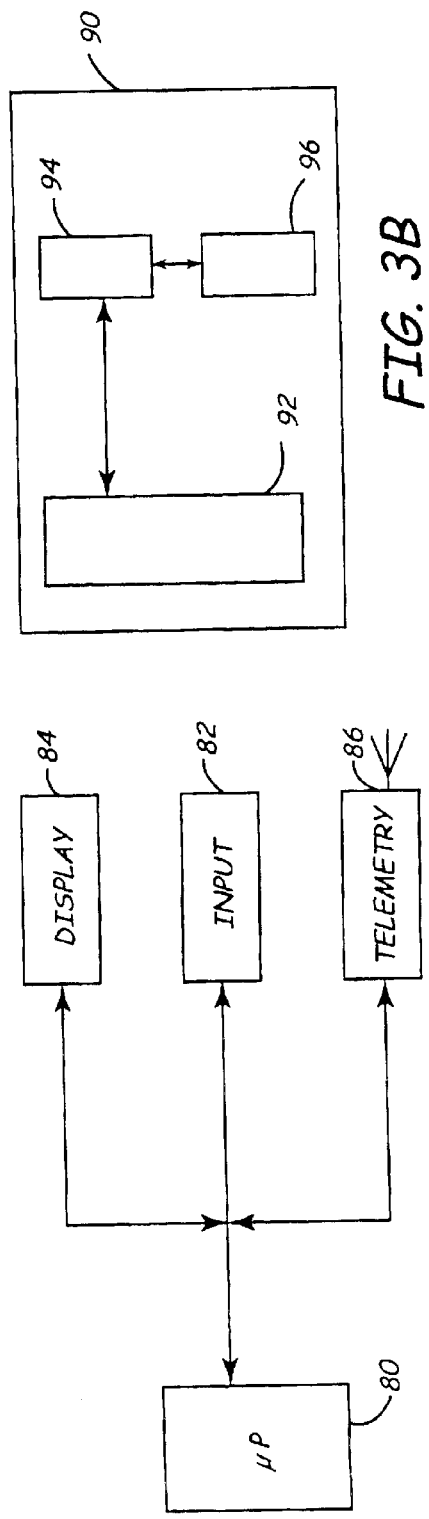
FIG. 3B
FIG. 3A

COMMUNICATIONS SYSTEM FOR AN IMPLANTABLE DEVICE AND A DRUG DISPENSER

This is a continuation of application Ser. No. 09/475,709, filed Dec. 30, 1999, now U.S. Pat. No. 6,471,645.

THE FIELD OF THE INVENTION

The present invention relates to implantable medical devices (IMDs). Specifically, the invention pertains to a remote bi-directional communications between the IMDs and a drug dispenser. More specifically the invention pertains to a closed loop system in which the IMDs monitor and determine the presence of a specific drug dose in the patient's body to send instructions to the drug dispenser or an interface medical unit (IMU) to implement a drug management scheme based on the monitored data. More specifically, the invention provides a dynamic drug management system in which the drug dose is chronically monitored by the IMDs to enhance drug effectiveness and as well monitor patient compliance with recommended drug administration regimen. The invention preferably utilizes a robust communication system integrated with a remote expert data center in a web-enabled environment to transmit the IMDs' data to a physician for evaluation and review thereby enhancing the delivery of therapy and clinical care remotely.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide a seamless system of remote patient diagnostics, care and medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Further, if the patient with the IMDs is taking a drug, it is often clinically prudent to monitor the dose and its impact on the patient and, as well, on the IMDs. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and contemporaneous procedures relating to an IMD uplink with, for example, a programmer. It is required that the report contain the identification of all the medical devices involved in any interactive procedure. Specifically, all peripheral and major devices that are used in down linking to the IMD need to be reported. Currently, such procedures are manually reported and require an operator or a medical person to diligently enter data during each procedure. One of the limitations of the problems with the reporting procedures is the fact that it is error prone and requires rechecking of the data to verify accuracy.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices. As is often the case, patients with multi-implanted medical devices may take a variety of medications. It is therefore necessary to monitor drug intake and its effect on the oprerational and functional parameters of the IMDs. More importantly, chronic monitoring of drug intake and its effect on the physiological and clinical conditions of the patient enables a proactive intervention to change the course of an otherwise serious medical condition. Thus, there is a need to monitor drug delivery and effectiveness via IMDs.

Accordingly it is vital to have a drug dispenser unit that would establish a communication system with IMDs. The unique position of IMDs enables a real-time assessment of physiological conditions which may change or indicate a measurable variance due to drug dose and delivery. IMDs could be adapted to provide measurements relating to the physiological impact of drug therapy. Further, IMDs could be adapted to provide a quick evaluation of the effectiveness of a drug to support a clinical decision as to whether a given dose is a prudent course of therapy.

The proliferation of patients with multi-implant medical devices worldwide has made it imperative to provide remote services to the IMDs and timely clinical care to the patient. Frequent use of programmers to communicate with the IMDs and provide various remote services, consistent with co-pending applications titled "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881; "Implantable Medical Device Programming Apparatus Having An Auxiliary Component Storage Compartment," filed Nov. 4, 1999, Ser. No. 09/433,477; which are all incorporated by reference herein in their entirety, has become an important aspect of patient care. Thus, in light of the referenced disclosures, communication with IMDs enhances the delivery of therapy and clinical care in real time. Specifically, as the number of patients with IMDs increases globally, the need to manage drug delivery and intake remotely becomes an economic imperative. Further, IMDs which are communicable and operable in a web-enabled environment, as contemplated by the cited disclosures hereinabove, provide a unique platform to assess the efficacy of drugs and the compliance of patients with prescribed regimens. Further, it is vital to have a drug dispenser that is adapted to have data communications with the IMDs and other data centers to support the remote patient management system contemplated by the present invention.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, including the programmer, with a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD. Further, in light of the present invetion, the Funke patent does neither suggest nor disclose the communications system between the IMD and a drug dispenser to monitor and assess the effectiveness of the dose based on the physiological status of the patient.

Yet another example of drug management based on smart drug dispenser units is disclosed by Martindale et al in U.S. Pat. No. 4,360,125 issued on Nov. 23, 1982. In the disclosure, a medication dispenser in which medication to be dispensed is housed including a member operable to allow medication access. The dispenser provides a medication alert signal at preselected times in accordance with a desired medication regimen. A medication access signal is provided when medication access is obtained. Data representative of the relative timing between a medication alert signal and a medication access signal is written into readable memory whereby that data is available to a physician for evaluation. In the preferred embodiment, the data is representative of the time of occurrence of each medication alert signal and medication access signal. The interval between medication alert signals is selectively alterable.

Further, examples of drug management based on smart drug dispensers are disclosed in U.S. Pat. Nos. 4,768,176; 4,768,177; 5,200,891; 5,642,731; 5,752,235 and 5,954,641 all to Kehr et al. Generally all the patents relate to a drug dispensing system with various alert features to monitor and manage the administration of medication and medical treatment regimens. None of these patents suggest or disclose a communication between the drug dispensing systems and an IMD.

Yet another prior art reference provides a multi-module medication delivery system as disclosed by Fischell in U.S. Pat. No. 4,494,950 issued Jan. 22, 1985. The disclosure relates to a system consisting a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external pill dispenser which is in wireless communications with IMDs. Further, the system does neither teach nor disclose an external programmer for telemetrically interacting with the pill dispenser.

Accordingly, it would be advantageous to provide a pill dispenser that communicates with IMDs to implement an effective drug management system. Yet another desirable advantage would be to provide a high speed communications scheme to enable the transmission of high fidelity sound, video and data to advance and implement efficient remote drug management of a clinical/therapy system via a programmer thereby enhancing patient clinical care. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via an associated external medical device, preferably a programmer, located in close proximity to the IMDs. The IMDs are adapted to communicate with a pill dispenser to monitor and log pill deposition and effectiveness. Some of the most significant advantages of the invention include the use of various communications media between the remote web-based expert data center and the programmer to remotely exchange clinically significant information and ultimately effect real-time drug intake and prescriptive changes as needed.

One of the many aspects of the present invention includes a real-time access of a programmer or a pill dispenser to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to the IMDs, as needed.

Yet another feature of the invention includes a communications scheme that provides a highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communications system. However, it should be noted that the communication systems, in the context of this invention, are interchangeable and may relate to various schemes of cable, fiber optics, microwave, radio, laser and similar communications or any practical combinations thereof.

Some of the distinguishing features of the present invention include the use of a robust web-based expert data center to collect drug therapy information based on data communication between the IMDs, the pill dispenser and the programmer. Specifcally the invention enables remote evaluation of drug performance in a patient. Although the present invention focuses on the remote real-time monitoring and management of drug therapy information, the system could advantageously be used to monitor clinical trials of drugs or collect clinical data relating to drug interaction or physiological impact of various doses on the patient.

Yet one of the other distinguishing features of the invention includes the use a highly flexible and adaptable communications scheme to promote continuous and real-time communications between a remote expert data center, a programmer and a pill dispenser associated with a plurality of IMDs. The IMDs are structured to share information intracorporeally and may interact with the programmer or the pill dispenser as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the data center via the programmer or pill dispenser by up linking the IMDs as needed.

The invention provides significant compatibility and scalability to other web-based applications such as telemedicine and emerging web-based technologies such as tele-immersion. For example, the system may be adapted to webtop applications in which a webtop unit may be used to uplink the patient to a remote data center for drug information exchange between the IMDs and the remote expert data center. In these and other web-based similar applications the data collected, in the manner and substance of the present invention, may be used as a preliminary screening to identify the need for further intervention using the advanced web technologies.

More significantly, the invention provides a system and method to remotely monitor drug effectiveness in a patient. Further, the invention enables a chronic evaluation of drugs in a patient on real time basis. The significance of this method includes the fact that the data collected in this manner could be used to influence the course of drug therapy.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 2 is a block diagram representing the major components of an IMD;

FIG. 3A is a block diagram presenting the major components of a programmer;

FIG. 3B is a block diagram representing a laser transceiver for high speed transmission of voice, video and other data;

DESCRIPTION OF THE PREFERRED EMBODIMENTS

Figure 1:
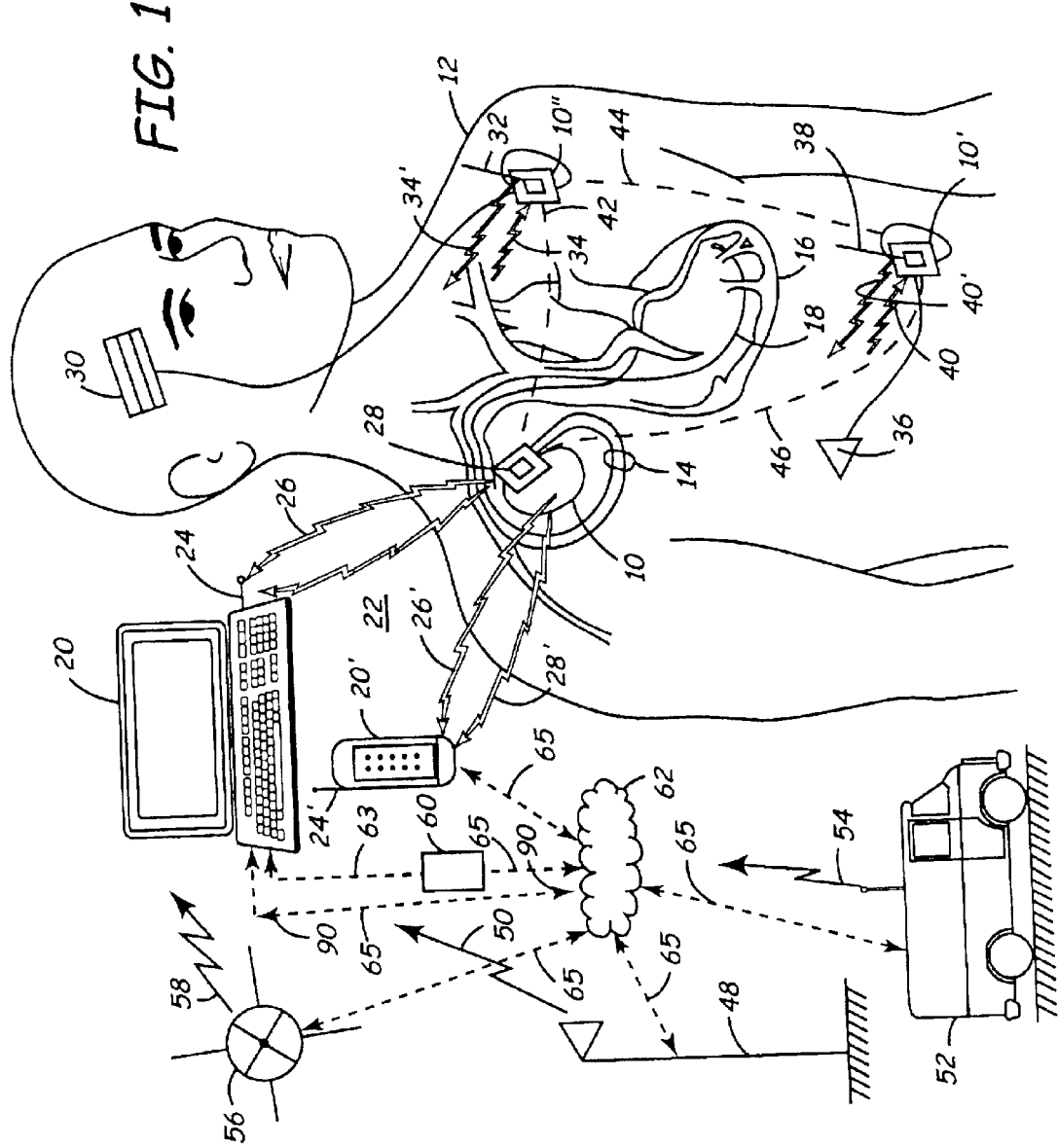
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, pill dispenser 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 3 0, and 3 6 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10"via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and pill dispenser 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or webtop unit 20'. Accordingly programmer 20 and webtop unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or pill dispenser 20' and data center 62. The communications link between Programmer 20 or pill dispenser 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, pill dispenser 20', mobile vehicle 52 and satellite 56 are in communications with data center 62 via wireless link 65. Further, mobile system 52 and satellite 56 are in wireless communications with programmer 20 or pill dispenser 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10, 10', 10" (which relates to neural implant 30) can be implemented to up-link, via wireless antenna 26', 28', 34', 34' 40, 40' or wireless antenna 24 of cellular phone 20', any one, two or more IMDs to programmer 20. Preferably bluetooth chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets arid architecture, transmitting at relatively high speed, to provide data, sound and video services on demand.

FIG. 2 illustrates typical components of an IMD, such as those contemplated by the present invention. Specifically, major operative structures common to all IMDs 10, 10' and 10" are represented in a generic format. In the interest of brevity, IMD 10 refers to all the other IMDs. Accordingly, IMD 10 is implanted in patient 12 beneath the patient's skin or muscle and is electrically coupled to heart 16 of patient 12 through pace/sense electrodes and lead conductor(s) (denoted by reference numeral 14 in FIG. 1) of at least one cardiac pacing lead 18 in a manner known in the art. IMD 10 contains therapy 1 monitor 70, timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 78 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction via suitable telemetry circuitry 78. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of realtime ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real-time data. Display screen 84 may also display plinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit is located proximate to programmer 20 or pill dispenser 20'. Data transmission between remote data center 62 and programmer unit 20 is executed via wave units 90. Typically, the first wave unit 90 accepts data and splits it into unique wavelength for transmission. The second wave unit recomposes the data back to its original form.

Figure 4A:
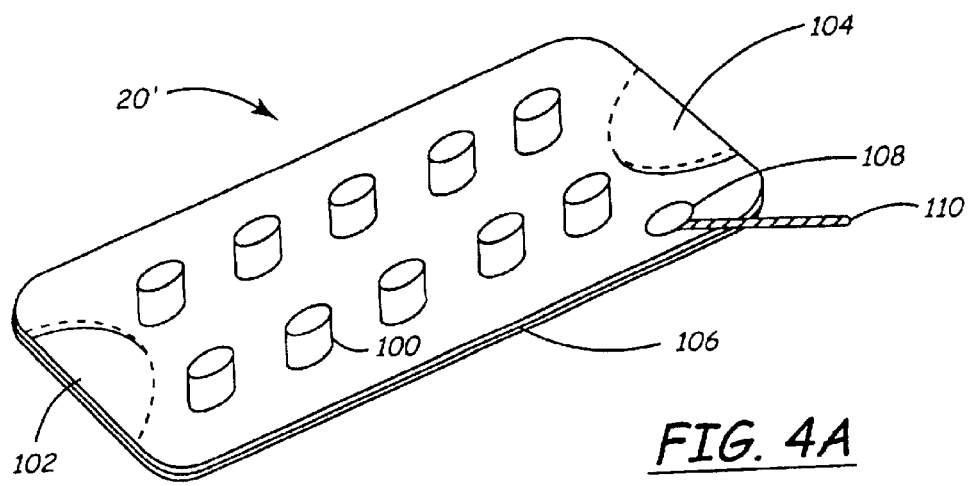
FIGS. 4A, 4B and 4C illustrate a perspective view, a side view and a schematic for the drug dispensing unit or interface medical unit, respectively.
Figure 4B:
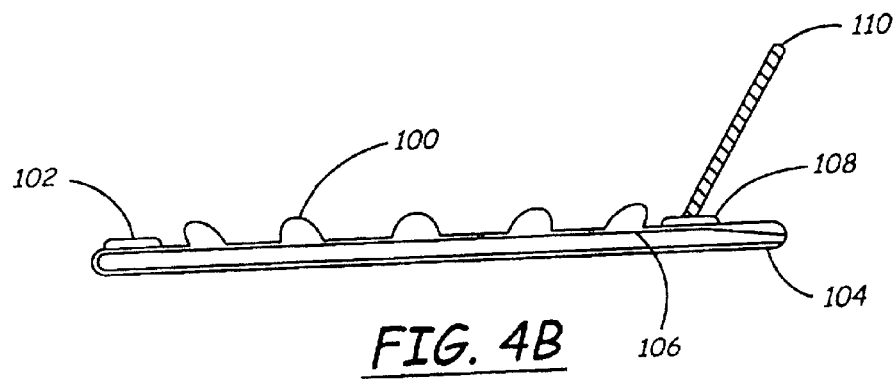
Figure 4C:
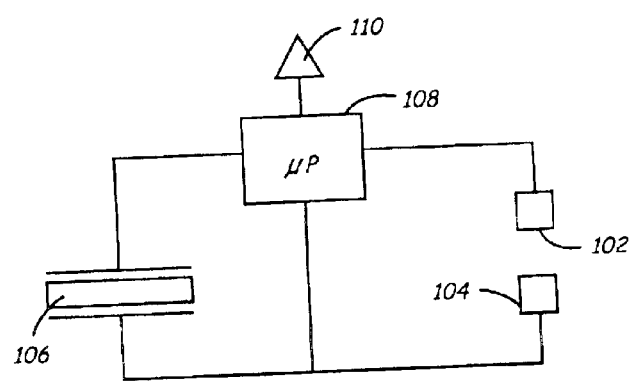

FIGS. 4A, 4B and 4C represent various views of pill dispenser unit 20'. The structure includes pill containers 100 that protrude upwards from the surface for pill or drug containment. The structure also includes upper metalized layer 102, superimposed on a plastic cover and lower metalized layer 104 superimposed on a plastic cover. Piezo-electric film 106 is disposed between the upper and the lower metalized layers. Further, microprocessor 108 is embedded between the upper and the lower layers. Telemetric antenna 110 is in electronic communications with microprocessor 108 and extends outward proximate therefrom.

Pill container 100 includes an indicator for the absence or presence of a pill in containers 100. Pill dispenser unit 20' is in preferably telemetric or equivalent wireless communications with IMDs 10, 10' and 10". In the alternate, pill dispenser unit 20' is in data communications with programmer 20.

Figure 5:
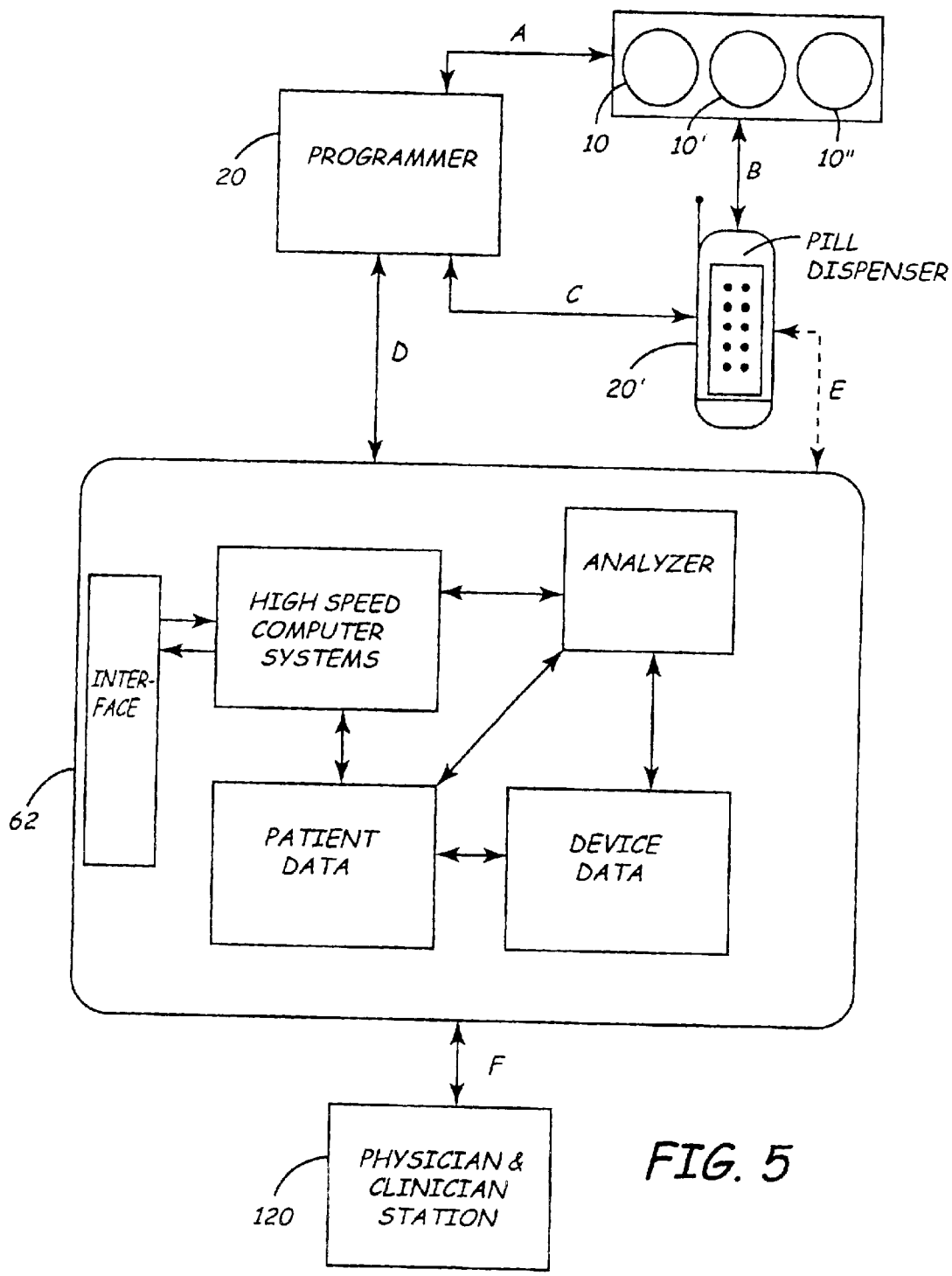
FIG. 5 is a block diagram representing the major data centers and the communication scheme according to the present invention.

Referring to FIG. 5, a communication scheme between remote data center 62, physician station 120 and programmer 20 and/or pill dispenser unit 20'. As indicated hereinabove, data center 62 includes high-speed computers and is preferably web enabled to provide remote access. Communication links A, B, C, D, E and F are preferably wireless although any other communication system such as cable, fiber-optics or equivalent could be implemented.

Generally, the present invention provides drug delivery and management primarily based on the chronic communications between pill dispenser unit 20' and IMDs 10, 10' and 10". Specifically, IMDs 10, 10' and 10" include a software program which would monitor the number of pills in pill dispenser 20' via link B which is equivalent to telemetry 110. In the alternate, the number of pills in dispenser 20' may be tracked via link C which establishes the communication between pill dispenser 20' and programmer 20. Pill dispenser 20' includes means for indicating the pill deposition from the package or container. Further IMDs 10, 10' and 10" include means for monitoring the deposition of the pills. A prescribed therapy schedule is preferably preprogrammed in the memory of IMDs 10, 10' and 10". The actual pill deposition in container 100 is known and correlates to one or more of the parameters programmed in IMDs 10, 10' and 10". Thus, the actual pill removal is assumed to be a precursor of administration of the pill by the patient consistent with the prescribed regimen. The relevant marker designating the time, dosage, and the type of medication is generated within a various diagnostic tables, and trend curves representing different physiologic parameters.

Further, IMDs 10, 10' and 10" chronically monitor the physiologic parameters of the patient and may alert the patient in cases, for example, when the drug does not influence a trend curve, causes the trends curve to oscillate, patient is not following the prescribed regimen or patient stops taking the medication altogether. Subsequently, IMDs 10, 10' and 10" could alert the physician or clinician to confer with the patient. This may be done via programmer 20 up-linking to data center 62. The Physician at station 120 will be able to access the patient data from data center 62. As shown in FIG. 5, Pill dispenser 20' is in data communication with data center 62. Thus the status of pill dispenser 20' is registered in either device or patient databases for the clinician to investigate.

Pill dispenser 20' is generally structured with a plurality of metal;lic layers such as 102 and 104, preferably aluminum and plastic layers. Thus pill dispenser 20' is a capacitor cell. Piezoelectric film 106 is similar to commercially available Kynar or equivalent, sandwithced between the two layers. Accordingly, whenever the patient manipulates pill dispenser 20' to break container 100 and remove a pill, a voltage will be produced within the piezoelectric film. This voltage may be used as a signal to the IMDs indicating the removal of a pill. Specifically, the signal being different from ECG, EMG, EMI or any other body generated signal, is suited to be used as a signal from pill dispenser 20' to IMDs 10. 10' and 10". IMDs 10, 10' and 10" may be programmed to identify this signal as an indication that the seal has been opened and that a pill has been injested by the patient. In the alternate, pill dispenser 20' may be used as a capacitor in a resonant circuit. Under this approach, when the patient presses the pill dispenser 20' the impendance is changed due to the skin-metal impedance change and consequently the resonanace circuit may be closed by the patient's hands. Accordingly, IMDs 10, 10' and 10" are able to monitor dose data and related clinical parameters by communicating with pill dispenser 20'. The measurements performed by IMDs 10, 10' and 10" are specific to the type of preprogrammed criteria and determinants thereof. However, in the context of the present invention, IMDs 10, 10' and 10" could be programmed to monitor a given pill dispenser 20' on a chronic basis. This will provide a stream of data that will indicate whether the patient has been following a prescribed dose and regimen. Further, IMDs 10, 10' and 10" may be programmed to monitor the efficacy of the drug by monitoring the physiological effects of the drug on the patient. Accordingly, a direct, real time assessment and interpretation of clinical status is obtained under the communication scheme advanced by the present invention.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus, also coupled to a graphics circuit, which is used to point to various locations on a screen/display to display menu choices for selection by the user or an alphanumeric keyboard for entering text or numbers and other symbols as shown in the above-incorporated '362 patent. Various touch-screen assemblies are known and commercially available. The display and or the keyboard of programmer 20, preferably include means for entering command signals from the operator to initiate transmissions of downlink telemetry from IMDs and to initiate and control telemetry sessions once a telemetry link with one or more IMDs has been established. The graphics display/screen is also used to display patient related data and menu choices and data entry fields used in entering the data in accordance with the present invention as described below. The graphics display/screen also displays a variety of screens of telemetered out data or real-time data. Programmer 20 is also provided with a strip chart printer or the like coupled to interface controller module so that a hard copy of a patient's ECG, EGM, marker channel or similar graphics display can be generated. Further, Programmer 20's history relating to instrumentation and software status may be printed from the printer. Similarly, once an uplink is established between programmer 20 and any one of IMDs 10, 10' and 10", various patient history data and IMD performance data may be printed out. The IMDs contemplated by the present invention include a cardiac pacemaker, a defibrillator, a pacer-defibrillator, implantable monitor (Reveal), cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy.

Data center 62 represents a high speed computer network system having wireless bi-directional data, voice and video communications with programmer 20 and/or pill dispenser 20' via wireless communications link 136. Generally data center 62 is preferably located in a central location and is preferably equipped with high-speed web-based computer networks. Preferably, data center 24 is manned 24-hours by operators and clinical personnel who are trained to provide a web-based remote service to programmer 20 and/or pill dispenser 20'. In accordance with the present invention, data center may be located in a corporate headquarters or manufacturing plant of the company that manufactures programmer 20. The wireless data communications link/connections can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, bidirectional wireless communications D , E and F act as a direct conduit for information exchange between remote data center 62 and programmer 20, pill dispenser 20' and physician center 120, respectively. Further, bi-directional wireless communications A and B provide an indirect link between remote data center 62 and IMDs 10, 10' and 10" via programmer 20 and pill dispenser 20'. In the context of this disclosure the word "data" when used in conjunction with bi-directional wireless communications also refers to sound, video and information transfer between the various centers.

Generally, in the context of the invention, all programmers located proximate to IMDs or patients with IMDs and distributed globally are connected to an expert data center to share software upgrades and access archived data. The programmer functions as an interface between the remotely located expert data center and the IMDs. Further, procedural functions such as monitoring the performance of the IMDs, upgrading software in the IMDs, upkeep and maintenance of the IMDS and related functions are implemented via the programmer. The preferably telemetric and yet local interaction between the programmer and the IMDs needs to be managed by a qualified operator. In order to facilitate the just-in-time patient care at the location of the patient, the invention provides pill dispenser 20' that is preferably wirelessly linked to data center 62. This scheme enables the dissemination of drug related clinical information worldwide while maintaining a high standard of patient care at reduced costs.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A drug delivery and management system in chronic communication between a pill dispenser and at least one implanted medical device (IMD) comprising:
    means for monitoring the number of pills in a pill dispenser;
    means for indicating pill deposition from a container in said pill dispenser;
    means for monitoring the deposition of the pills incorporated in an implanted medical device;
    means for preprogramming a drug therapy regimen implemented in said implanted medical device; and
    means for chronically monitoring and alerting a patient when said drug does not influence a trend curve.

2. The system of claim 1 wherein said means for monitoring the number of pills includes a microprocessor.

3. The system of claim 2 wherein said means for monitoring the number of pills further includes a telemetric antenna in communication with said microprocessor.

4. The system of claim 1 wherein said means for indicating pill deposition includes a piezoelectric film.

5. The system of claim 1 wherein one of a voltage signal and impedance change is used to monitor the number of pills in the pill dispenser.

6. A capacitor cell forming a pill dispenser having wireless communication between at least one implanted medical device and external devices, including a remote database center, the combination comprising:
    the pill dispenser having a piezoelectric film;
    means for sensing breakage of a container incorporated in said capacitor cell;
    means for producing a signal when a pill is removed from the pill dispenser, said signal being different from ECG, EMG, EMR or other body-generated signal;
    means for identifying the signal as an indication that a seal has been opened and that a pill has been ingested by a patient; and
    means for chronically monitoring the pill dispenser in conjunction with the patient's physiological data and reaction thereof.

7. The combination of claim 6 wherein said means for sensing breakage includes one of a voltage signal and impedance change to sense breakage of a container.

8. The combination of claim 6 wherein said means for producing a signal when a pill is removed from said container includes means for confirming breakage of a layer.

9. The combination of claim 7 wherein said means for sensing breakage includes means for transferring a signal to the at least one implanted medical device to trigger a timer to monitor pill ingestion by the patient.

* * * * *